United States Patent
Abou Shousha

(10) Patent No.: US 12,357,172 B2
(45) Date of Patent: Jul. 15, 2025

(54) VISUAL FIELD MAP EXPANSION

(71) Applicant: Heru Inc., Miami, FL (US)

(72) Inventor: Mohamed Abou Shousha, Fort Lauderdale, FL (US)

(73) Assignee: Heru Inc., Miami, FL (US)

( * ) Notice: Subject to any disclaimer, the term of this patent is extended or adjusted under 35 U.S.C. 154(b) by 807 days.

(21) Appl. No.: 17/538,862

(22) Filed: Nov. 30, 2021

(65) Prior Publication Data

US 2023/0165460 A1 Jun. 1, 2023

(51) Int. Cl.
| | |
|---|---|
| A61B 3/113 | (2006.01) |
| A61B 3/00 | (2006.01) |
| G06F 3/01 | (2006.01) |
| G06F 3/14 | (2006.01) |
| G06T 3/40 | (2024.01) |

(52) U.S. Cl.
CPC ............... *A61B 3/113* (2013.01); *A61B 3/005* (2013.01); *A61B 3/0091* (2013.01); *G06F 3/013* (2013.01); *G06F 3/14* (2013.01); *G06T 3/40* (2013.01)

(58) Field of Classification Search
CPC ........... A61B 3/145; A61B 3/14; A61B 3/032; A61B 3/0285; A61B 3/028; A61B 3/024; A61B 3/113; A61B 3/005; A61B 3/0091; G06F 3/013; G06F 3/14; G06F 3/011; G06F 3/012; G06F 3/1446; G06T 3/40; G06T 15/20
USPC ......................................................... 351/210
See application file for complete search history.

(56) References Cited

U.S. PATENT DOCUMENTS

| | | | |
|---|---|---|---|
| 10,722,114 B1 | 7/2020 | Berme et al. | |
| 10,827,918 B1 * | 11/2020 | Nuriel | ................ A61B 3/08 |
| 2010/0073469 A1 | 3/2010 | Fateh | |
| 2013/0147686 A1 | 6/2013 | Clavin et al. | |
| 2016/0377864 A1 | 12/2016 | Moran et al. | |
| 2018/0249151 A1 * | 8/2018 | Freeman | ................ G16H 40/63 |

FOREIGN PATENT DOCUMENTS

WO 2015-108887 A1 7/2015

OTHER PUBLICATIONS

International Search Report and Written Opinion issued in corresponding International Application No. PCT/US2022/080523 on Mar. 21, 2023 (8 pages).

* cited by examiner

*Primary Examiner* — Travis S Fissel
(74) *Attorney, Agent, or Firm* — Foley & Lardner LLP

(57) ABSTRACT

A method includes obtaining spatial information indicating positions of electronic displays relative to a wearable device and selecting a first display location on an electronic display other than a wearable display of the wearable device based on the spatial information indicating that the first display location on the electronic display corresponds to a first field location of a visual field. The method further includes selecting a second display location on the wearable device based on the spatial information indicating that the second display location on the wearable display corresponds to a second field location of the visual field. The method further includes causing presentation of (i) a first stimulus at the first display location on the electronic display and (ii) a second stimulus at the second display location on the wearable device and generating ocular anomaly information based on feedback information related to the presented stimuli.

20 Claims, 6 Drawing Sheets

VISUAL FIELD MAP EXPANSION

BACKGROUND

A wearable device can be used to perform vision testing to determine vision defects and eye-related conditions by testing the visual field of an eye over a series of characteristics. For example, the wearable device may present visual stimuli on a portion of its display, where the presentation includes changing the locations of visual stimuli over the wearable device display and measuring eye responses to the stimuli.

SUMMARY

In the context of vision testing using a wearable device, hardware limitations may reduce the user interface region of the wearable device in which visual stimuli may be presented. The reduced-size region may be less than the total visual field of a user's eye. Such size limitations may reduce the total area of a visual field that can be detected, especially the visual field of an eye associated with peripheral vision. These hardware limitations may prevent vision testing of certain areas of a user's peripheral vision due to this loss in the testable size of a viewable region.

In some embodiments, a wearable device may perform operations to update ocular anomaly information for an eye by presenting stimuli at field locations of a visual field of the eye. The wearable device may obtain spatial information indicating the position, orientation, or other spatial information of a set of electronic displays relative to a wearable device. Some embodiments may include instructions to test a field location and determine whether an eye can see stimuli presented at the field location. After selecting the field location, a wearable device or a computer connected to the wearable device may then use the obtained spatial information to select an electronic display to present a first stimulus at a display location mapped to the field location. Either at the same time or at a different time, the wearable device may present a second stimulus on a display of the wearable device, where the display may include a waveguide or another type of display to present the second stimulus to an eye. During or after the presentation of the stimuli, the wearable device may collect eye-related characteristics or other feedback information with an eye-tracking sensor or other types of sensors. Some embodiments may then generate ocular anomaly information indicating one or more ocular anomalies based on the collected feedback information indicating whether or not the eye responded to the presentation of the stimuli.

Various other aspects, features, and advantages of the invention will be apparent through the detailed description of the invention and the drawings attached hereto. It is also to be understood that both the foregoing general description and the following detailed description are examples, and not restrictive of the scope of the invention. As used in the specification and in the claims, the singular forms of "a," "an," and "the" include plural referents unless the context clearly dictates otherwise. In addition, as used in the specification and in the claims, the term "or" means "and/or" unless the context clearly dictates otherwise. Additionally, as used in the specification, "a portion" refers to a part of, or the entirety of (i.e., the entire portion), a given item (e.g., data) unless the context clearly dictates otherwise. Furthermore, a "set" may refer to a singular form or a plural form, such as that a "set of items" may refer to one item or a plurality of items.

DETAILED DESCRIPTION

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

Figure 1A:
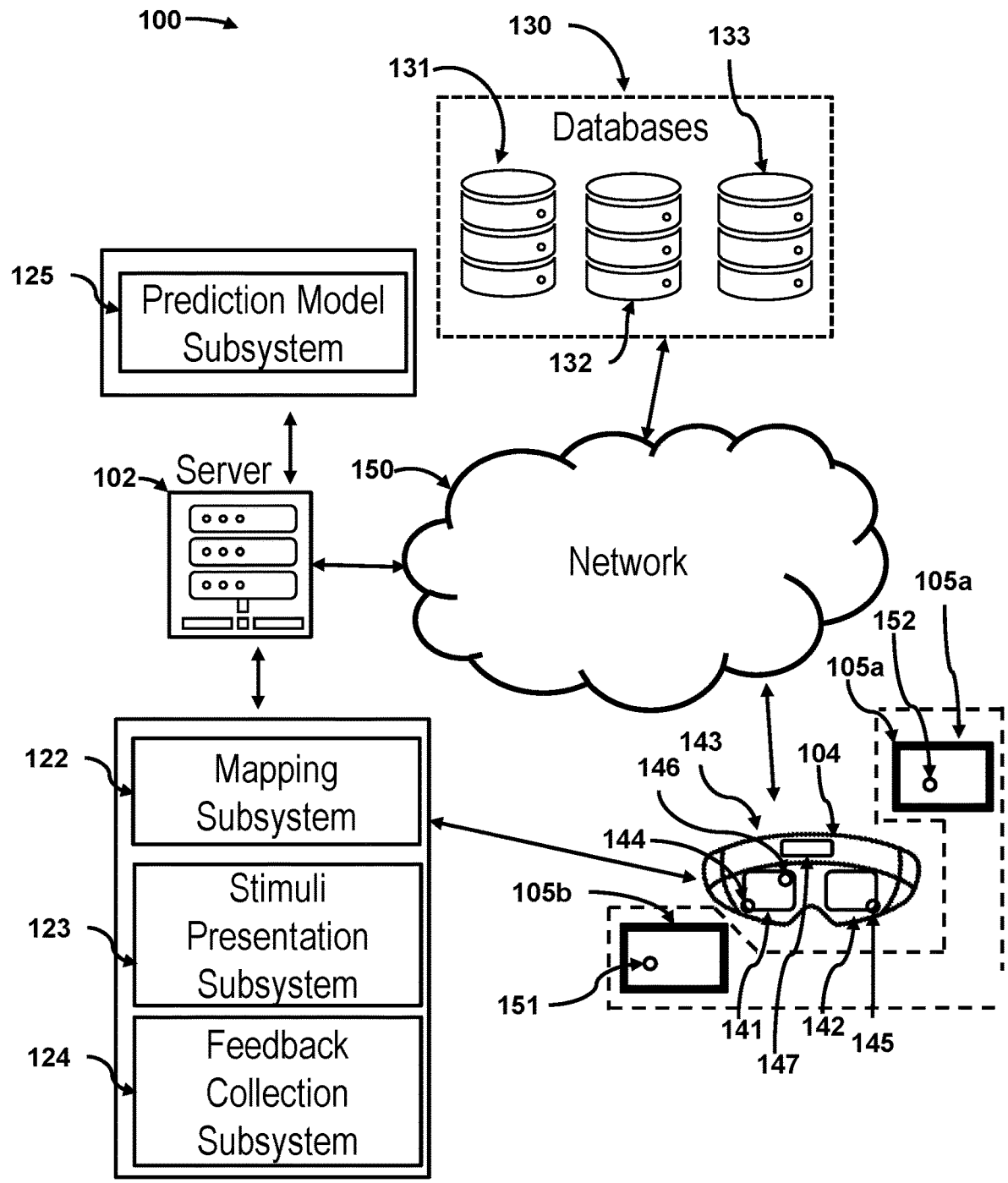
FIG. 1A illustrates a system for facilitating vision testing and collecting feedback information, in accordance with one or more embodiments.

FIG. 1A illustrates a system for facilitating vision testing and collecting feedback information, in accordance with one or more embodiments. In some embodiments, system 100 may include a server 102 (or other computer system 102), where such system 102 may include one or more non-transitory storage media storing program instructions to perform one or more operations of a mapping subsystem 122, a stimuli presentation subsystem 123, or a feedback collection subsystem 124. In some embodiments, the system 100 includes a wearable device 104, where the wearable device 104 may include one or more non-transitory storage media storing program instructions to perform one or more operations of the mapping subsystem 122, the stimuli presentation subsystem 123, or the feedback collection subsystem 124. The system 100 may also include a set of external displays 105 (e.g., accessories of the wearable device 104, desktop monitors, television screens, or other external displays), where the set of external displays 105 may be provided instructions to display visual stimuli based on measurements or instructions provided by the wearable device 104 or the server 102. In some embodiments, the wearable device 104 may communicate with various other electronic devices via a network 150, where the network 150 may include the Internet, a local area network, a peer-to-peer network, etc.

The wearable device 104 may send and receive messages through the network 150 to communicate with a server 102, where the server 102 may include one or more non-transitory storage media storing program instructions to perform one or more operations of a prediction model subsystem 125. It should further be noted that, while one or more operations are described herein as being performed by particular components of the system 100, those operations may be performed by other components of the system 100 in some embodiments. For example, operations described in this disclosure as being performed by the server 102 may instead be performed by the wearable device 104, where program code or data stored on the server 102 may be stored on the wearable device 104 or another client computer device instead. Similarly, in some embodiments, the server 102 may store program code or perform operations described as being performed by the wearable device 104. For example, the server may perform operations described as being performed by the mapping subsystem 122, the stimuli presentation subsystem 123, or the feedback collection subsystem 124. Furthermore, although some embodiments are described herein with respect to machine learning models, other prediction models (e.g., a statistical model) may be used instead of or in addition to machine learning models. For example, a statistical model may be used to replace a neural network model in one or more embodiments to determine an ocular anomaly.

In some embodiments, the system 100 may present a set of stimuli (e.g., shapes, text, or images) on a display of the wearable device 104. The wearable device 104 may include a housing 143, a left transparent display 141, and a right transparent display 142, where light may be projected from emitters of the wearable device through waveguides of the transparent displays 141-142 to present stimuli viewable by an eye(s) of a user wearing the wearable device 104. The wearable device 104 also includes a set of outward-facing sensors 147, where the set of outward-facing sensors 147 may provide sensor data indicating the physical space around the wearable device 104. In some embodiments, the set of outward-facing sensors 147 may include cameras, infrared sensors, lidar sensors, radar sensors, etc.

Furthermore, the system 100 may present stimuli on the set of external displays 105 during a visual testing operation. While the set of external displays 105 is shown with two external displays, a set of external displays may include more or fewer external displays, such as only one external display or more than two external displays. For example, a set of external displays may include four external displays, eight external displays, nine external displays, or some other number of external displays. The external displays may include one or more types of electronic displays, such as computer monitors, smartphones, television screens, laptop devices, tablet devices, LED devices, LCD devices, other types of electronic displays, etc. In some embodiments, the external display may include a projector, where the location of the external display may include a wall or screen onto which one or more stimuli is projected. In some embodiments, the external display may itself be transparent or partially transparent.

During or after a visual testing operation, the system 100 may obtain feedback information related to the set of stimuli, where the feedback information may indicate whether or how an eye responds to one or more stimuli of the set of stimuli. For example, some embodiments may use the wearable device 104 to collect feedback information that includes various eye-related characteristics. In some embodiments, the feedback information may include an indication of a response of an eye to the presentation of a dynamic stimulus at a first display location 146 on a wearable device 104. Alternatively, or in addition, the feedback information may include an indication of a lack of a response to such a stimulus. The response or lack of response may be determined based on one or more eye-related characteristics, such as an eye movement, a gaze direction, a distance in which an eye's gaze traveled in the gaze direction, a pupil size change, a user-specific input, etc.

In some embodiments, the feedback information may include image data or results based on image data. For example, some embodiments may obtain an image or sequence of images (e.g., in the form of a video) of an eye captured during a testing operation as the eye responds to a stimulus. The image of the eye may be an image of a retina of the eye, such as an image of the overall retina or a portion thereof, an image of a cornea of the eye, such as an image of the overall cornea or a portion thereof, or another eye image. As used in this disclosure, a wearable display location may include a display location of a wearable device.

In some embodiments, the system 100 may detect one or more ocular anomalies of an eye and update associated ocular anomaly information based on feedback information indicating eye responses to stimuli. In some embodiments, an ocular anomaly may include a visual field defect, eye misalignment, anomalies in pupil movement or size, etc. For example, some embodiments may use a prediction model to detect a non-responsive region of a visual field or another ocular anomaly of a visual field portion associated with the ocular anomaly. In some embodiments, a region associated with an ocular anomaly may be determined by a selection of locations or regions of an eye's visual field that fail to satisfy one or more vision criteria. In some embodiments, satisfying a set of vision criteria for a visual field location may include determining whether an eye responded to a stimulus presented at the display location mapped to the visual field location, where different presented stimuli may vary in brightness, color, shape, size, etc.

In some embodiments, data used or updated by one or more operations described in this disclosure may be stored in a set of databases 130. In some embodiments, the server 102, the wearable device 104, the set of external displays 105, or other computer devices may access the set of databases to perform one or more operations described in this disclosure. For example, a prediction model used to determine ocular anomaly information may be obtained from a first database 131, where the first database 131 may be used to store prediction models or parameters of prediction models. Alternatively, or in addition, the set of databases 130 may store feedback information collected by the wearable device 104 or results determined from the feedback information. For example, a second database 132 may be used to store a set of user profiles that include or link to feedback information corresponding with eye measurement data for the users identified by the set of user profiles. Alternatively, or in addition, the set of databases 130 may store instructions indicating different types of testing procedures. For example, a third database 133 may store a set of testing instructions that causes a first stimulus to be presented on the wearable device 104, then causes a second stimulus to be presented on a first external display 105a, and thereafter causes a third stimulus to be presented on a second external display 105b.

Subsystems 122-125

In some embodiments, the mapping subsystem 122 may generate a field-to-display map that maps a position or region of a visual field with a position or region of the set of external displays 105 or of an AR interface displayed on the left transparent display 141 or the right transparent display 142. The field-to-display map may be stored in various forms, such as in the form of a set of multi-dimensional arrays, a function, a subroutine, etc. For example, the field-to-display map may include a first multi-dimensional array, where the first two dimensions of the first array may indicate a coordinate in a combined display space that maps 1:1 with a visual field. In some embodiments, a third dimension of the first array may identify which external display or wearable display to use when presenting a stimulus. Furthermore, a fourth and fifth dimension of the array may be used as coordinates relative to an origin of each respective external display. In some embodiments, an array or other set of numbers described in this disclosure may instead be divided into a plurality of arrays or other subsets of numbers. In some embodiments, the field-to-display map may be used in reverse, such that a display location may be mapped to a visual field location ("field location") using the field-to-display map. Some embodiments pre-generate a display-to-field map by inverting one or more of the arrays described above. Furthermore, some embodiments may use or update a map by using an array or other data structure of the map. Various other embodiments of the field-to-display map are possible, as described elsewhere in this disclosure.

In some embodiments, the mapping subsystem 122 may obtain sensor information from the set of outward-facing sensors 147, where the sensor information may include position measurements of the set of external displays 105. For example, a user wearing the wearable device 104 may rotate or translate their head, which may cause a corresponding rotation or translation of the wearable device 104. Some embodiments may detect these changes in the physical orientation or position of the wearable device 104 with respect to the set of external displays 105. Some embodiments may then perform a mapping operation to determine the positions and orientations of the set of external displays based on the sensor information collected by the set of outward-facing sensors 147.

In some embodiments, the mapping subsystem 122 may update a field-to-display map that stores or otherwise indicates associations between field locations of a visual field and display locations of the left transparent display 141, the right transparent display 142, or the set of external displays 105. For example, the set of outward-facing sensors 147 may include one or more cameras to collect visual information from a surrounding area of the wearable device 104, where the visual information may be used to determine a position or orientation of one or more devices of the set of external displays 105. As the wearable device 104 is moved, some embodiments may continuously obtain sensor information indicating changes to the external environment, including changes in the position or orientation of the set of external displays 105 relative to the position or orientation of the wearable device 104. For example, some embodiments may generate a point cloud representing the surfaces of objects around the wearable device 104 and determine the positions and orientations of the set of external displays 105 relative to the wearable device 104 based on the point cloud. Furthermore, some embodiments may continuously update the field-to-display map as new sensor information is collected by the set of outward-facing sensors 147.

In some embodiments, the stimuli presentation subsystem 123 may present a set of stimuli on the wearable device 104 or the set of external displays 105. In some embodiments, the left transparent display 141 and right transparent display 142 may be positioned with respect to the housing 143 to fit an orbital area on a user such that each display of the transparent displays 141-142 is able to collect data and present stimuli or other images to the user. The left transparent display 141 and right transparent display 142 may contain or be associated with an electronic display configured to present re-created images to an eye viewing the respective transparent display. In various embodiments, electronic display may include a projector, display screen, and/or hardware to present an image viewable by the eye. In some embodiments, a projector of an electronic monitor may be positioned to project images onto an eye of the subject or onto or through a screen, glass, waveguide, or other material. For example, the stimuli presentation subsystem 123 may cause a fixation point or another visual stimulus to be projected onto the first display location 146, where the fixation point at the first display location 146 may then be viewed by an eye of a user wearing the wearable device 104.

In some embodiments, the stimuli presentation subsystem 123 may cause a set of stimuli to be displayed onto electronic displays other than the displays of the other external displays, such as an external display of the set of the external displays 105. For example, after presenting a stimulus on a display of the wearable device 104, the stimuli presentation subsystem 123 may cause a stimulus to be presented on the second external display 105b at a second display location 151. As used in this disclosure, an external display location may include a display location on an external display. The stimuli presentation subsystem 123 may then proceed to display additional stimuli on an additional location of the first external display 105a, the wearable device 104, or the second external display 105b.

Some embodiments may determine the display location for a stimulus by first determining the location or region of a visual field. After determining the location or region of the visual field, some embodiments may then use a field-to-display map to determine which display location of the left transparent display 141, the right transparent display 142, or the set of external displays 105 to use when displaying a stimulus. For example, some embodiments may determine that a previous sequence of sensor measurements indicated that a first region of a visual field has not yet been tested and select this first region for testing. Some embodiments may then use the field-to-display map to determine a third display location 152 on the first external display 105a and, in response to selecting the third display location 152, display a stimulus at the third display location 152. As described elsewhere in this disclosure, some embodiments may measure eye movements or otherwise measure responses of an eye to the stimuli presented on the set of external displays 105 to measure a visual field of the eye. Furthermore, as described in this disclosure, a visual field location of a stimulus may include the field location mapped to or otherwise associated with the display location of the stimulus, where the mapping or association between the display and the field location is determined by a field-to-display map. Similarly, as used in this disclosure, a gaze location that is located at a field location may also be described as being located at a display location mapped to the field location.

In some embodiments, the feedback collection subsystem 124 may record feedback information indicating eye responses to the set of stimuli presented on the wearable device 104 or the set of external displays 105. In some embodiments, the transparent displays 141-142 may include a left inward directed sensor 144 and a right inward directed sensor 145, where the inward directed sensors 144-145 may include eye-tracking sensors. The inward directed sensors 144-145 may include cameras, infrared cameras, photodetectors, infrared sensors, etc. For example, the inward directed sensors 144-145 may include cameras configured to track pupil movement and determine and track visual axes of the subject. In some embodiments, the inward directed sensors 144-145 may include infrared cameras and be positioned in lower portions relative to the transparent displays 141-142. The inward directed sensors 144-145 may be directionally aligned to point toward a presumed pupil region for line-of-sight tracking or pupil tracking.

In some embodiments, the feedback collection subsystem 124 may use the inward directed sensors 144-145 to collect feedback information indicating eye motion as an eye responds to different stimuli. For example, the feedback collection subsystem 124 may retrieve feedback information of an eye collected by the inward directed sensors 144-145 as the eye responds to the presentation of a stimulus at the first display location 146 and the second display location 151. By collecting feedback information while stimuli are presented on both the wearable device 104 and one or more devices of the set of external displays 105, some embodiments may increase the boundaries of a visual field for which ocular anomalies may be detected.

In some embodiments, the prediction model subsystem 125 may retrieve stimuli information, such as stimuli locations and characteristics of the stimuli locations, where the stimuli locations may include locations on the set of external displays 105. The prediction model subsystem 125 may also retrieve training outputs indicative of the presence or absence of ocular anomalies, such as visual defect information, defect categories, or other outputs of a prediction model. The prediction model subsystem 125 may then provide the set of stimuli information and training outputs to a machine learning model to update the parameters of the machine learning model to predict ocular anomalies based on new inputs. Alternatively, or in addition, the prediction model subsystem 125 may use statistical models or rules to determine ocular anomalies and generate a visual field map representing a visual field of an eye, where one or more regions of the visual field map may be associated with a set of ocular anomalies or otherwise include ocular anomaly information.

Figure 1B:
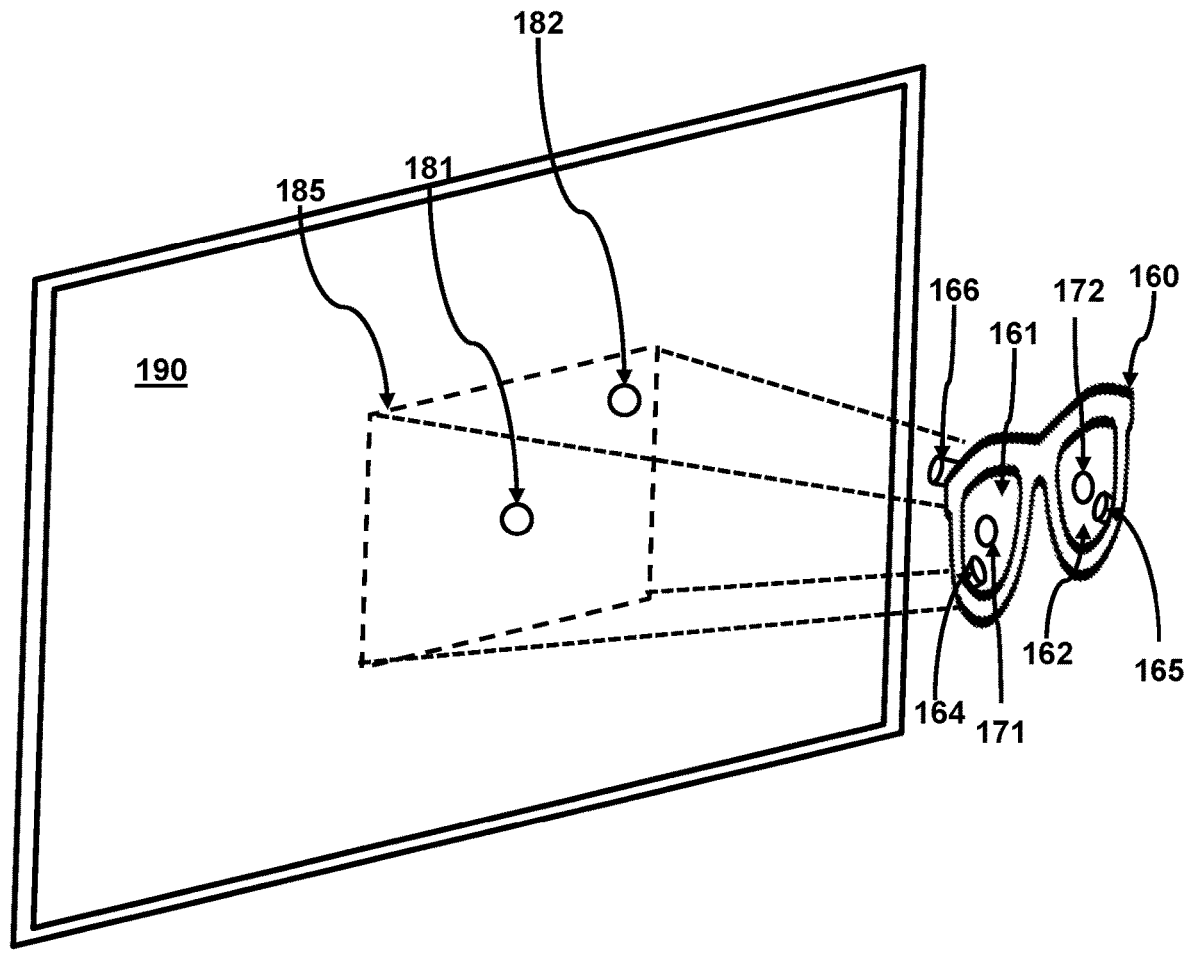
FIG. 1B illustrates a vision testing environment of a user, in accordance with one or more embodiments.

FIG. 1B illustrates a vision testing environment of a user, in accordance with one or more embodiments. The vision testing environment includes an external display 190. The external display 190 may present images, text, video, etc. to a user wearing the wearable device 160. In some embodiments, the wearable device 160 may include a left transparent lens 161 and a right transparent lens 162. Some embodiments may permit a user wearing the wearable device 160 to look through the lenses 161-162 to see a first visual stimulus at first display location 181 and a second stimulus at a second display location 182, where the presentation of the stimuli may occur concurrently or in series. Alternatively, in some embodiments, a wearable device may leave the regions covered by the lenses 161-162 empty, such that an eye may see through the empty space and view images presented on the external display 190.

The wearable device 160 may include a left inward-facing sensor 164 or a right inward-facing sensor 165. Some embodiments may use the inward-facing sensors 164-165 to collect eye-related sensor information while stimuli are presented on the external display 190. For example, the inward-facing sensors 164-165 may track the gaze location and pupil dilation of a user's eyes as the eye shifts its focus from a stimulus positioned at the first display location 181 to a stimulus presented at the second display location 182. In some embodiments, an outward-facing sensor 166 may include a visual spectrum camera or infrared camera to collect information about the environment in front of the wearable device 160. The outward-facing sensor 166 may collect environmental information that includes images or videos of the region 185, where a rotation or translation of the wearable device 160 may cause a corresponding change in the shift in what is displayed in the region 185. In some embodiments, the outward-facing sensor 166 or some other component of the wearable device 160 may include additional sensors, such as an accelerometer or gyroscope, where the sensor information may be used to determine a position and orientation of the external display 190 relative to the wearable device 160.

As described elsewhere, some embodiment may use the sensor information collected by the sensors 164-166 to update a field-to-display map. For example, the wearable device 160 may transmit the sensor information collected by the sensors 164-166 to another computer system, such as the server 102. The server 102 may then perform a mapping operation that includes updating a field-to-display map to determine which field position of the visual field map to associate with display locations of the external display 190. The server 102 may then use the mapping operation to update a visual field map based on eye-related sensor information collected by the sensors 164-165 and the updated field-to-display map.

In some embodiments, the left transparent lens 161 or right transparent lens 162 may include an LED panel, OLED panel, or waveguide to display shapes, text, images, or other stimuli to a user wearing the wearable device 160. Furthermore, the inward facing sensors 164-165 may capture eye-related sensor information as a user's eye responds to the presentation of stimuli on the wearable device 160 or the display 190. For example, some embodiments may activate a display of the wearable device 160 to present a stimulus at display locations 171-172 on the lenses 161-162 and then display a second stimulus at the second display location 182. During the presentation of the stimuli on the left and right transparent lenses 161-162, the sensors 164-165 may collect eye-related sensor information as the eye responds to the presentation of the stimuli.

Figure 2A:
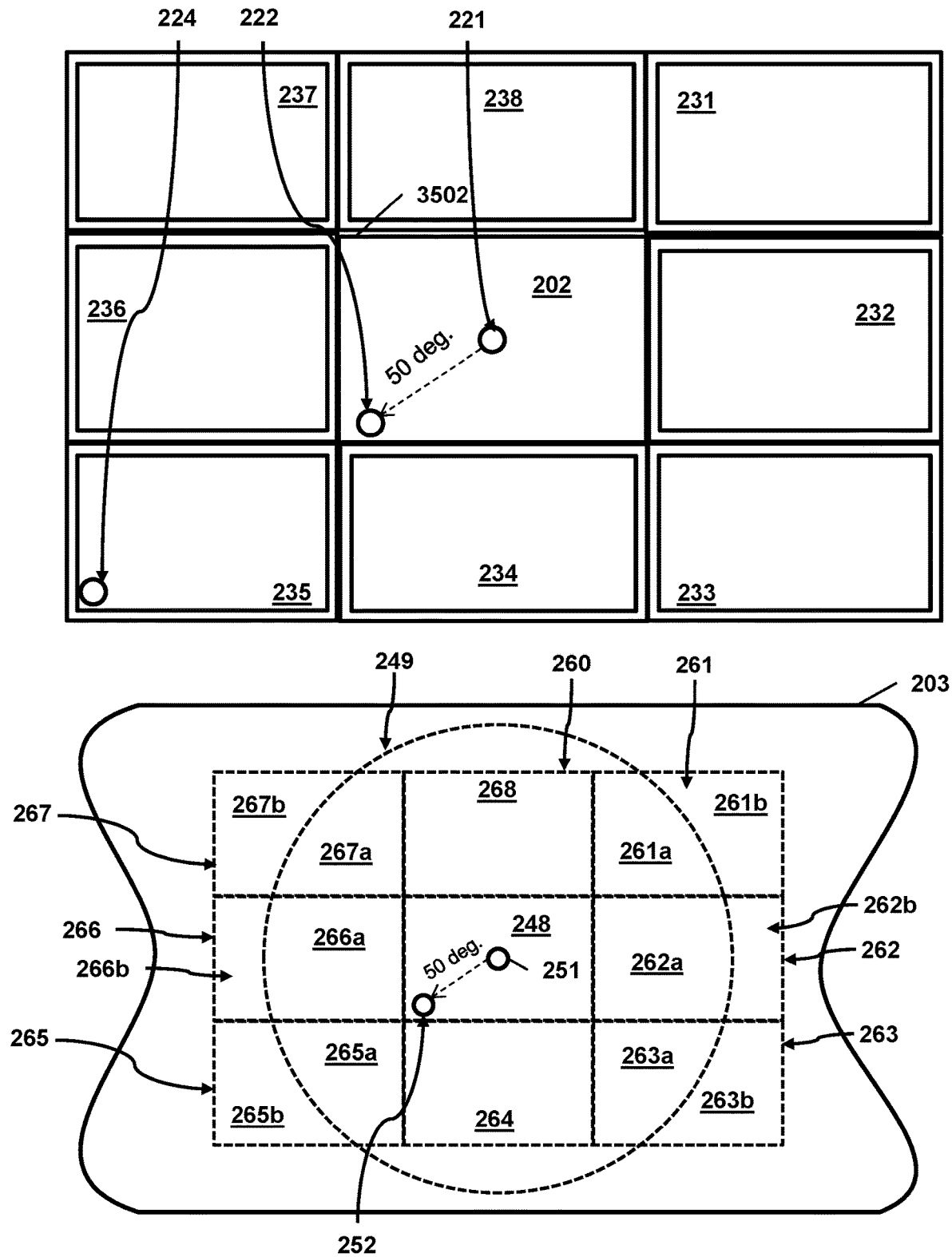
FIGS. 2A-2B illustrate vision testing involving monitoring eye movement in response to a set of presented stimuli, in accordance with one or more embodiments.
Figure 2B:
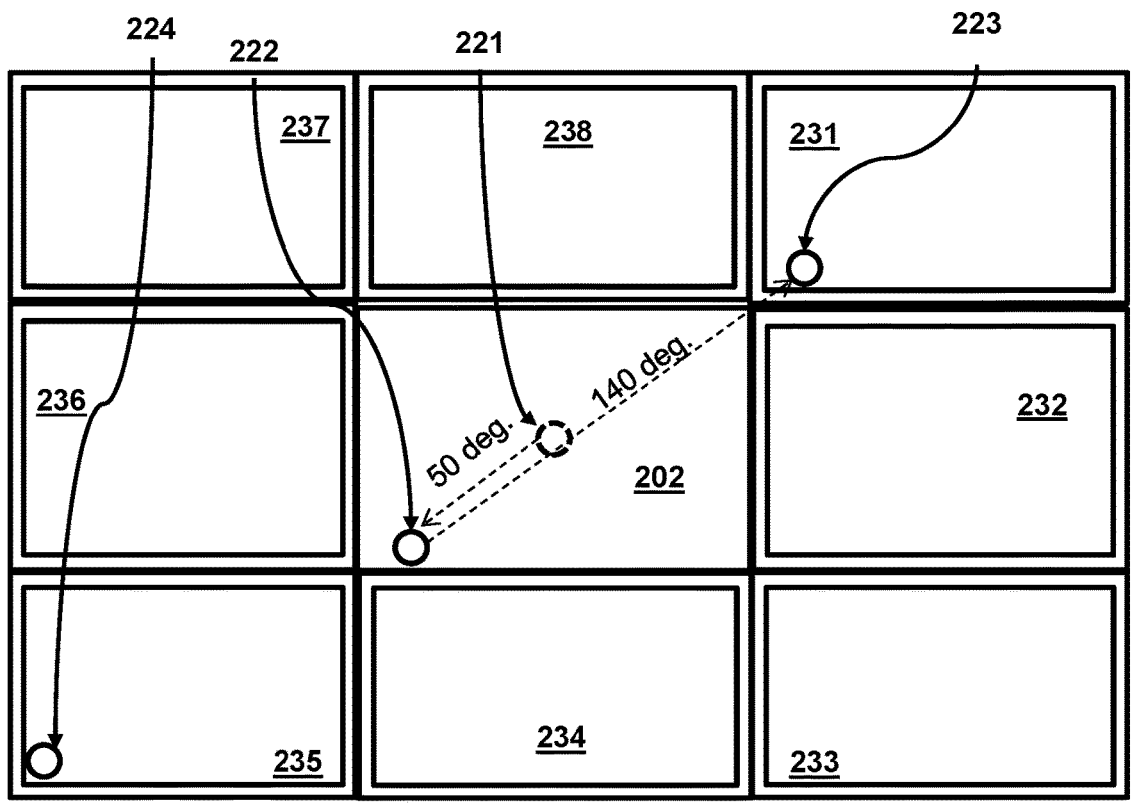
Figure 2B:
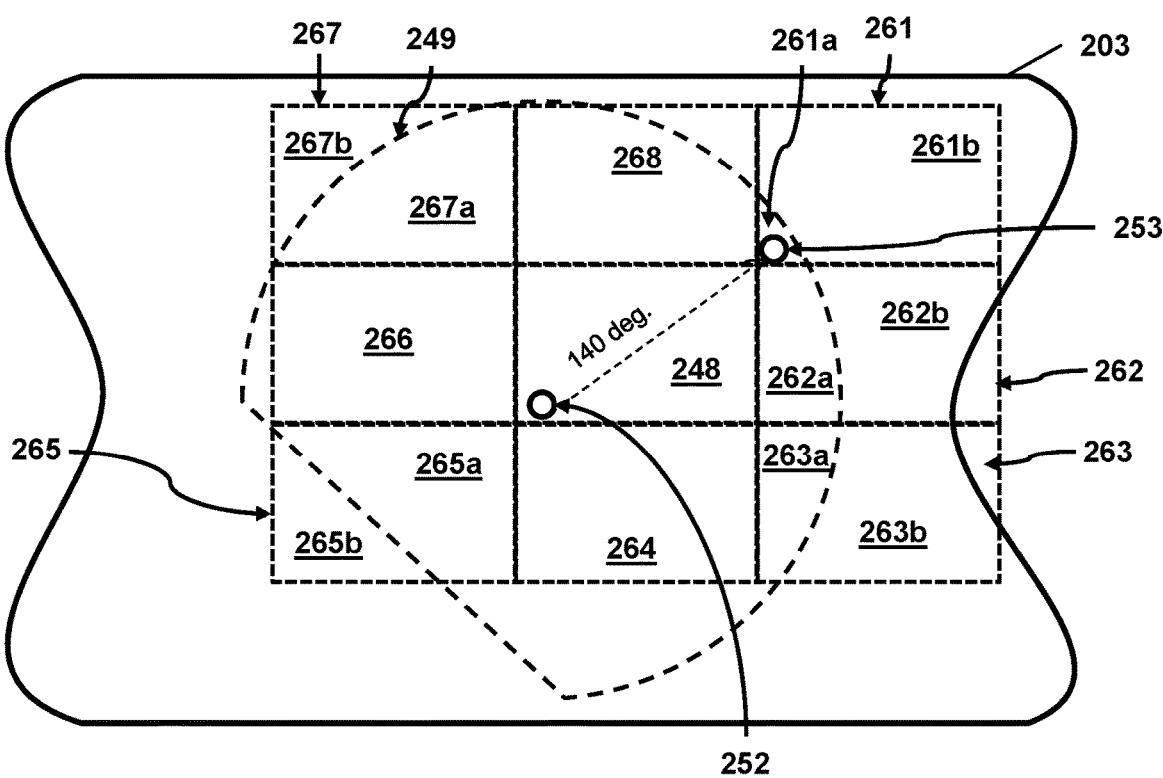

FIGS. 2A-2B illustrate vision testing involving monitoring eye movement in response to a set of presented stimuli, in accordance with one or more embodiments. In some embodiments, various stimuli may be presented concurrently or in sequence on an AR interface displayed on a wearable display 202 and a set of external displays 231-238, where an eye viewing the wearable display 202 may also be able to view stimuli displayed on the set of external displays 231-238. Some embodiments may use sensors to collect or otherwise track the characteristics of an eye as stimuli are presented to the eye. A characteristic of an eye may include limbus positions, gaze directions, gaze locations, the speed at which a gaze is changing, distance traveled from a previous gaze location, pupil sizes, physical responses to an appearance of a stimulus in a visual field, or other characteristics. For example, some embodiments may update a visual field map 203 representing the visual field of an eye by indicating a first visual field position where an eye moved in a gaze direction of a stimulus appearing at the visual field position.

In some embodiments, the sensors of a wearable device may include a set of sensors capable of collecting sensor information usable to form representation of the space around the wearable device. For example, the set of sensors may include cameras to collect image data, infrared sensors or LIDAR sensors to collect distance data, accelerometers to collect force data, gyroscopic sensors to collect rotation data, etc. The collected sensor data may be used to generate a spatial mapping using spatial mapping algorithms. For example, some embodiments may use an infrared sensor of a wearable device to collect infrared light emitted by the wearable device and determine the distance from an object using a time-of-flight algorithm. Alternatively, or in addition, the set of sensors may include various other types of depth sensors, such as structured light sensors or red-green-blue (RGB) depth sensors. Furthermore, some embodiments may track the position or location of a wearable device relative to a set of electronic displays using positioning algorithms, such as a simultaneous localization and mapping (SLAM) algorithm. In addition, some embodiments may receive sensor information from external sensors to increase the accuracy of a spatial mapping indicating the position or orientation of objects around a wearable device and the wearable device itself. For example, a system may use a set of outside-in sensors that project infrared light into a space and determine the position of a wearable device based on the reflection of the infrared light.

Some embodiments may use the collected sensor information to generate a map of external devices around the wearable device that indicates spatial information of the external devices relative to the device itself, where the map may associate a visual field location ("field location") of an eye's visual field with a display location of a display of the wearable device or an electronic display. In some embodiments, the field location may represent a position within the visual field of an eye or eyes of a user wearing the wearable device, and the map associating the field location with the display location may account for the orientation of the wearable device or the gaze location of the eye. For example, some embodiments may continuously update a field-to-display map by determining a map indicating an association between a set of positions representing the visual field of a user wearing the wearable device relative to the set of external displays 231-238. In some embodiments, each external display of the set of external displays 231-238 may be an electronic display that is physically unattached to a wearable device attached to the wearable display 202.

In some embodiments, the visual field of the user may be independent of eye movement, where the visual field is determined by default or by a set of calibration measurements. For example, a user may physically rotate or translate a wearable device (e.g., by rotating or translating their head), and the field-to-display map may be updated based on a measured change in the spatial mapping indicating updates to the position or orientation of objects around the wearable device. Furthermore, some embodiments may update the visual field based on changes in gaze locations. For example, some embodiments may include inward-facing sensors to measure an eye's gaze location in real time and determine a change in the visual field of the eye based on the gaze location.

Some embodiments may associate different regions of a visual field map with display regions of an external display or a wearable device display. For example, some embodiments may update the visual field map 203 to indicate a set of visual field regions 261-268 that maps to display regions of the set of external displays 231-238, respectively. For example, field locations within the visual field region 261 may map to display locations within a display region of the external display 231, field locations within the visual field region 262 may map to display locations within a display region of the external display 232, etc. Furthermore, the field-to-display map may associate a visual field region 248 at the center of the visual field map 203 to the wearable display 202. Some embodiments may set the boundary of each region as a stimuli boundary. For example, the dashed lines forming the visual field region 248 may represent a stimuli boundary of the visual field region 248.

In some embodiments, with respect to FIG. 2A, a first stimulus at the first display location 221 may be presented on the wearable display 202, where the wearable display 202 is attached to a wearable device. In some embodiments, the wearable display 202 may include a transparent display on which one or more stimuli may be presented. Alternatively, or in addition, the wearable display 202 may include an opaque display on which one or more stimuli may be presented. Alternatively, or in addition, the wearable display 202 may include a variable-transparency material. For example, the wearable display 202 may include switchable glass, where part or all of the wearable display 202 may be made opaque or transparent based on an electric voltage. A user's eye may respond to the presentation of the first stimulus at the first display location 221 by moving until a gaze is fixed at the first display location 221. During and after the presentation of the first stimulus at the first display location 221, a set of sensors of the wearable device may measure eye-related characteristics indicating the eye's response. For example, the set of sensors may obtain images of the eye to determine that the eye is focused on a first stimulus at the first display location 221.

Some embodiments may follow a visual field, to map testing operation and select a field location to test. Some embodiments may select a second field location 252 for testing. After selecting the second field location 252, some embodiments may use a field-to-display map to determine that a second stimulus should be displayed at a second display location 222 on the wearable display 202. In some embodiments, the second stimulus may then be presented at the second display location 222 of the wearable display 202. After the second stimulus is presented at the second display location 222, an eye that was previously fixed on the first stimulus at the first display location 221 may then move and focus on the second stimulus at the second display location 222. In some embodiments, the gaze direction of the eye may be tracked from the first field location 251 to the second field location 252. For example, after the appearance of the second stimulus at the second display location 222, the peripheral vision of an eye may detect the presence of the second stimulus at the second display location 222 despite the eye being fixed at the first display location 221. Based on the eye's response and the association between the second display location 222 and the second field location 252, some embodiments may determine that the eye is responsive to stimuli presented at the second field location 252 (e.g., and, thus, can see stimuli presented at such location). Alternatively, some embodiments may detect that the eye had moved from the first display location 221 in the direction of the second display location 222. The motion of the eye toward the second field location 252 may indicate that the peripheral vision of the eye corresponding with the second field location 252 is responsive even if the eye does not fix its gaze at the second display location 222. Alternatively, if the eye does not respond at all to the presentation of the second stimulus at the second display location 222 or performs motion that does not indicate that the user saw the second stimulus, some embodiments may update the visual field map 203 to indicate that there is a visual defect at the second field location 252.

As indicated in the visual field map 203, an eye may be associated with an ocular range 249 that represents a predicted maximum peripheral vision of the eye. As indicated by the visual field region 261, the visual field region 263, the visual field region 265, and the visual field region 267, each respective visual field region may be split into a first portion representing a visual field region that is predicted to be viewable within the ocular range 249 and a second portion representing a visual field region that is not viewable within the ocular range 249. For example, the visual field region 261 may be split into a viewable visual field sub-region 261a and a non-viewable visual field sub-region 261b. Similarly, some embodiments may divide the visual field region 263 into a viewable visual field sub-region 263a and a non-viewable visual field sub-region 263b. Similarly, some embodiments may divide the visual field region 265 into a viewable visual field sub-region 265a and a non-viewable visual field sub-region 265b. Similarly, some embodiments may divide the visual field region 267 into a viewable visual field sub-region 267a and a non-viewable visual field sub-region 267b. As described elsewhere in this disclosure, some embodiments may determine whether or not to select a field location for stimuli presentation based on whether or not the field location is within a viewable region. For example, some embodiments may initially select both a first field location within the viewable visual field sub-region 267a and a second field location within the non-viewable visual field sub-region 267b as candidate field locations for a visual test. Some embodiments may then filter out selected field locations in non-viewable sub-regions from the candidate field locations, removing the second field location from the list of possible future field locations for the visual test.

As shown in FIG. 2B, another stimulus may be presented at another display location of an external display while or after the second stimulus is presented after a gaze location is focused on the second display location 222. Some embodiments may then perform a testing operation that causes the system to test the third field location 253. Some embodiments may then use a field-to-display map to determine that the third field location 253 corresponds with a third display location 223, where the third display location 223 is a display location of the external display 231. As indicated in FIG. 2B, after a detected change in the gaze of the eye, some embodiments may update a field-to-display map to reflect the shift in the set of visual field regions 261-268 to indicate a change in the mapping. Furthermore, some embodiments may update a shape or size of the ocular range 249 to indicate a change in the viewable region.

Some embodiments may then display a third stimulus at the third display location 223. The angular distance traveled by an eye rotating from being fixed on the second stimulus displayed at the second display location 222 and the third stimulus displayed at the third display location 223 may be equal to 140 degrees, which may be a distance greater than the angular distance traveled by an eye focusing between two points at the corners of the AR interface shown on the wearable display 202. The feedback information measured from a user's eye as the eye moves its gaze from the second display location 222 to the third display location 223 may be used to update the visual field map 203 to indicate that the third field location 253 is viewable by a user. As described elsewhere in this disclosure, some embodiments may update the visual field map 203 to indicate that the visual field of the eye can detect visual changes corresponding with the third field location 253 even if the gaze of an eye moves its gaze direction toward the third field location 253 without actually reaching the third field location 253.

Some embodiments may present multiple stimuli concurrently. For example, some embodiments may present a first stimulus at the second display location 222 on a user interface of a wearable display and display multiple other stimuli on a plurality of external displays surrounding the visual field of the wearable display. Similarly, some embodiments may then remove or otherwise deemphasize one or more stimuli of the multiple other stimuli while the first stimulus remains displayed. As visual changes occur on the other display locations, the changes may cause an eye to move its gaze in the direction of the visual change. Alternatively, if the eye does not move in the gaze direction of the visual change, some embodiments may determine that the visual change occurred in a defective area of the eye's visual field. In some embodiments, the first stimulus may also temporarily disappear, flash, or otherwise visually change in a continual or continuous manner. Alternatively, or in addition, the first stimulus may disappear after a new stimulus is presented but may reappear in the same display location after the presentation of each new stimulus. For example, a stimulus may be presented at the first display location 221 to re-center the eye to a calibrated central position after each presentation of a stimulus at the display locations 222-223. By causing these changes to the first stimulus, the first stimulus may act as a calibration stimulus, where the eye may instinctively return to gaze on the first stimulus as a calibration measurement for other measurements.

Furthermore, some embodiments may display a plurality of stimuli such that at least one stimulus is presented on each external display of the set of external displays 231-238. As described elsewhere in this disclosure, some embodiments may collect feedback information during or after the presentation of each stimulus of the presented stimuli on the set of external displays 231-238 and the wearable display 202. Some embodiments may then generate or otherwise update the visual field map 203 based on the feedback information by determining which stimulus caused an eye to respond to its corresponding presentation and updating the visual field map 203 based on the field location associated with the stimulus.

Figure 3:
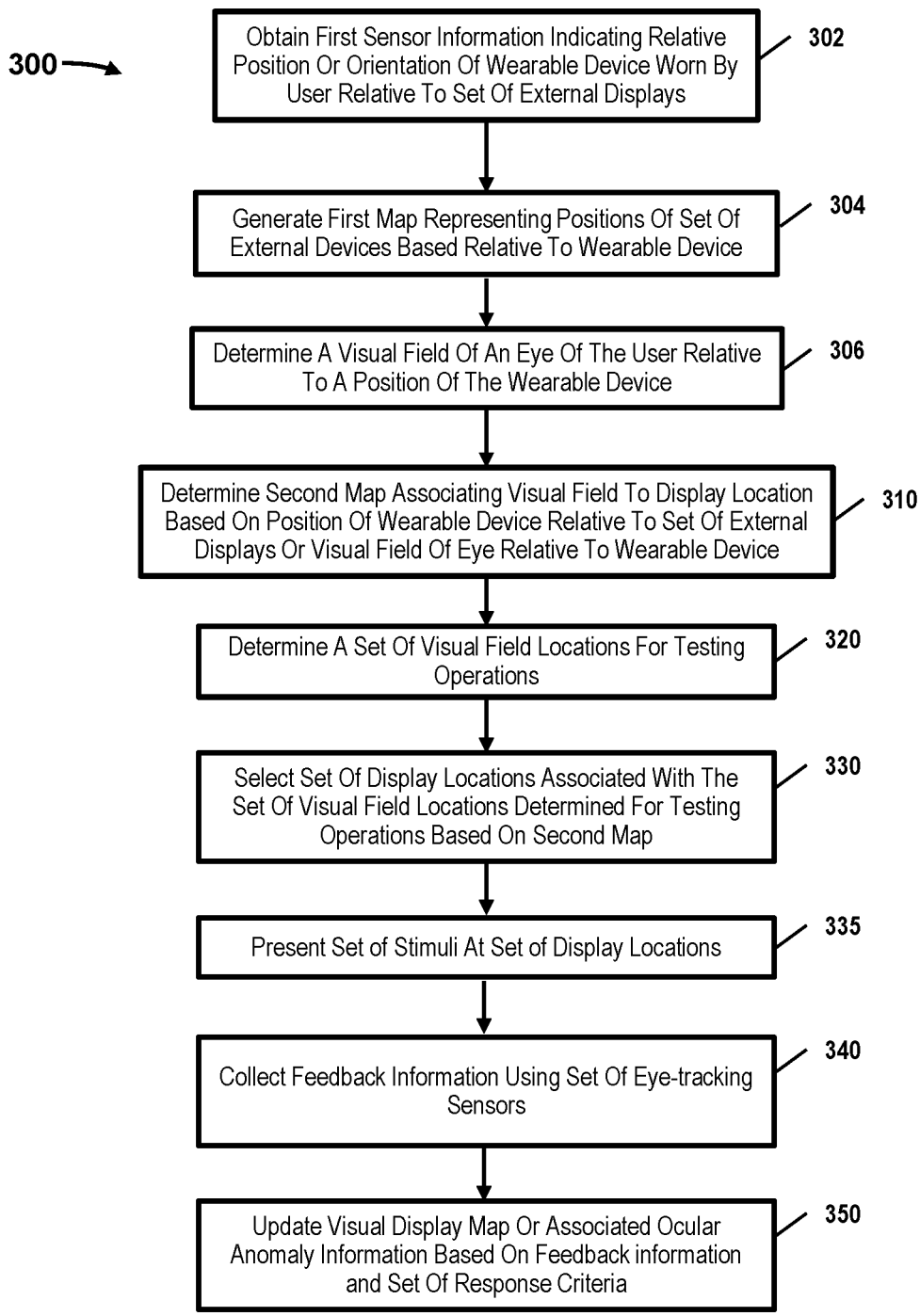
FIG. 3 shows a flowchart of a process to perform a visual test using multiple displays, in accordance with one or more embodiments.

FIG. 3 shows a flowchart of a process to perform a visual test using multiple displays, in accordance with one or more embodiments. Some embodiments may obtain first sensor information indicating relative position or orientation of a wearable device worn by a user relative to a set of external displays, as indicated by block 302 of the process 300. As described elsewhere in this disclosure, the first sensor information may include LIDAR measurements, radar measurements, image measurements, infrared measurements, accelerometer measurements, gyroscopic measurements, magnetic measurements, etc. Alternatively, or in addition, some embodiments may receive information from external sensors to provide position information indicating a position of the wearable device relative to a set of sensors or other objects.

Some embodiments may determine a distance or orientation of an external display by causing a set of calibration stimuli to be presented on the external display. Some embodiments may then use one or more sensors attached to a wearable device or sensors in communication with the wearable device to detect the set of calibration stimuli. Some embodiments may then determine a distance from each of the set of calibration stimuli based on the size or shape of the calibration stimuli. Some embodiments may then determine a position or orientation of an external display based on the set of distance measurements. For example, by determining the distances between the wearable device and each of the four corners of an external display, some embodiments may determine a distance and orientation of the external display relative to the wearable device using a set of geometric operations.

Some embodiments may generate a first map representing the positions of a set of external devices based on a position of the wearable device, as indicated by block 304 of the process 300. In some embodiments, the first map may be a field-to-display map directly used to determine either the display location to display a stimulus or a field location of a visual field based on a known display location. Alternatively, as described elsewhere in this disclosure, the first may be an intermediate map used to determine the field-to-display map.

Various operations may be performed to generate the first map. Some embodiments may be provided with a position or orientation of an external display relative to a wearable device by a user. For example, some embodiments may receive a first input from a user indicating that a wearable device is set at a first physical position (0, 0, 1), receive a second input from a user indicating that an upper-left corner of an electronic display other than the wearable display is at the position (10, 0.5, 2), and receive a third input indicating that a lower-right corner of the electronic display is at the position (10, −0.5, 1). In some embodiments, the coordinates may represent the position of the electronic display in meters in an x-direction, y-direction, and z-direction. Alternatively, or in addition, some embodiments may store or use coordinates in other coordinate system, such as spherical coordinates or cylindrical coordinates. Some embodiments may then generate or otherwise update a map indicating a display position and orientation of the electronic display relative to an objective position of the wearable device based on these inputs. Furthermore, some embodiments may use a field-to-display map to determine a field location from a display location.

Alternatively, or in addition, some embodiments may use spatial positioning algorithms, such as time-of-flight algorithms or a SLAM algorithm, to determine the position or orientation of a wearable device relative to a set of external displays. For example, some embodiments may perform real-time spatial mapping to obtain an array of positions indicating the objects around a wearable device using images provided by a set of cameras, accelerometer data, and infrared sensor data. The array of positions may be filtered to determine the location of displays. For example, some embodiments may determine a set of external displays using an object recognition model to recognize a known shape of the display, such as a rectangle bounded by a black border. Alternatively, or in addition, some embodiments may determine the location of external displays based on a set of known visual indicators displayed at the edges or background of the external displays. Some embodiments may then use the filtered set of positions or regions based on the filtered set of positions to determine a first map indicating display locations of the external displays with respect to the wearable device. Some embodiments may combine the first map with a set of known positions representing the display locations of a display of the wearable device to determine a map associating display locations relative to an objective position of the wearable device. In some embodiments, the objective position may include a calibrated position associated with the gaze location representing the center of a user's vision.

Some embodiments may determine a visual field of an eye of the user relative to a position of the wearable device, as indicated by block 306 of the process 300. The visual field of an eye may be centered around the gaze location of the eye, where the visual region surrounding the gaze location may include the peripheral vision of the eye. Some embodiments may use eye-tracking sensors to measure eye-movement vectors or other representations of eye-related characteristics. As described elsewhere in this disclosure, some embodiments may continuously measure a set of eye-related characteristics and perform one or more operations based on a determination that an eye-related characteristic satisfied a set of criteria based on gaze location, gaze direction, distance traveled in a gaze direction, a determination that another characteristic satisfied a threshold, etc.

Some embodiments may determine a second map associating the visual field to a display location based on the position of the wearable device relative to the set of external displays or the visual field of the eye relative to the wearable device, as indicated by block 310 of the process 300. Some embodiments may perform a matrix transformation operation by transforming a matrix of a first map to generate a second map. Alternatively, some embodiments may modify the result of a first function by using a rotation function based on the rotation of a wearable device or a translation of the wearable device. In some embodiments, the first map may store associations between display locations and field locations of a fixed visual field representing the front of a wearable device, and the second map may represent a rotation operator or translation operator indicating the rotation or translation of an eye relative to the calibrated center of the fixed visual field.

In some embodiments, the second map may be a field-to-display map. Some embodiments may dynamically update a field-to-display map based on changes to the configuration of an eye. For example, some embodiments may present a first stimulus at a first display location to fix the gaze of an eye at the first stimulus. Some embodiments may then simultaneously remove the first stimulus and add a second stimulus at a second display location. Some embodiments may then determine whether the eye has fixed its gaze at the second display location based on an updated feedback information provided by eye-tracking sensors and, in response to a determination that the eye has fixed its gaze at the second display location, update the field-to-display map by transforming the original field-to-display map based on the new gaze location of the eye relative to a reference gaze location.

While the above describes determining the map based on the visual field of the eye relative to the wearable device, some embodiments may determine the map without determining the gaze-updated visual field of the eye. For example, some embodiments may determine the map based on the position of the wearable device relative to the set of external displays.

Some embodiments may determine a set of field locations for testing operations, as indicated by block 320 of the process 300. In some embodiments, the set of field locations may be pre-selected. For example, some embodiments may have a pre-selected set of field locations to test, where each pre-selected field location is associated with a different region of a visual field. Some embodiments may then generate or otherwise obtain a candidate set of field locations for use as a set of stimuli locations.

Some embodiments may rank the candidate set of field locations to determine a field location sequence sorted by one or more ranking operations, where the highest ranked field location may be prioritized as the location at which a stimulus is presented. For example, some embodiments may rank the candidate set of field locations based on which field location is farthest from a set of tested field locations. Alternatively, some embodiments may rank the candidate set of field locations based on which field location is closest to a recognized ocular anomaly. For example, some embodiments may select a field location for testing based on a determination that the selected field location is closest to a visual defect that a user's eye had not previously responded to. Furthermore, as described elsewhere in this disclosure, some embodiments may determine the ranking in real time using data obtained from an eye-tracking device, such as a pupil or eye tracker or other eye-tracking device.

Some embodiments may select testing locations using a random or pseudorandom value, where the random value may be determined based on a physical sensor and the pseudorandom value may be determined based on a pseudorandom algorithm. For example, some embodiments may determine a visual field distance from a previously tested field location, where the visual field distance may exceed or otherwise satisfy a distance threshold. Some embodiments may determine a first set of testing locations and then select a next field location from the first set of testing locations based on the random or pseudorandom value. By using a random or pseudorandom selection process, some embodiments may prevent a user's pattern-learning behaviors from affecting the accuracy of a visual field map.

Some embodiments may dynamically determine a future field location to test based on a result of a previous test. For example, based on a determination that a first field location is associated with a detected defective area or another type of ocular anomaly, some embodiments may determine whether the first field location is near a stimuli boundary of the display region in which the first field is presented. Based on a determination that the first field location is within the distance threshold of the stimuli boundary, some embodiments may select a second visual field position or region associated with the field position for future presentation. As described elsewhere in this disclosure, some embodiments may then present the second stimulus on an external display at an external display location mapped to the second visual field position by a field-to-display map and collect additional feedback information. Based on the collected additional feedback information, some embodiments may modify the size or shape of the detected defective area or other ocular anomaly.

Some embodiments may select a set of display locations associated with the set of field locations determined for testing operations based on the second map, where the second map associates the set of display locations with the set of field locations, as indicated by block 330 of the process 300. For example, some embodiments may obtain a first field location represented by the polar coordinates [0.5, 0.5], representing the polar coordinates of a visual field to test. Some embodiments may then select a display location by using a field-to-display map by determining the display location associated with the polar coordinates [0.5, 0.5]. In some embodiments, the polar coordinates [0.5, 0.5] may be transformed to a modified set of polar coordinates based on the rotation of an eye. For example, some embodiments may determine that an eye is focused on the polar coordinates [0.1, 0.1] relative to a fixed front vector of a wearable device. Some embodiments may then modify the polar coordinates based on the eye's gaze location and update the polar coordinates to be [0.6, 0.6]. Some embodiments may then determine the display location mapped to the polar coordinates [0.6, 0.6]. As described elsewhere in this disclosure, some embodiments may determine a field location sequence.

Some embodiments may present a set of stimuli at the set of display locations, as indicated by block 335 of the process 300. In some embodiments, a stimulus presented at a display location may include a static fixation point, such as a black or red dot. Alternatively, or in addition, stimulus presented at a display location may include an animation, a picture, a character, a symbol, etc. In some embodiments, the stimuli presented on a plurality of displays may be scaled to account for distances between displays. For example, some embodiments may obtain a sequence causing the presentation of a first red circle to appear on an external display and a second red circle to appear on a wearable device display. Some embodiments may then determine a stimulus length to scale one red circle based on the other. For example, some embodiments may determine a distance between the wearable device and the external display and proportionally increase the size of the stimulus presented on the external display such that the stimulus on the external display appears the same size as the stimulus on the wearable device display.

Some embodiments may collect feedback information using a set of eye-tracking sensors, as indicated by block 340 of the process 300. In some embodiments, the feedback information may indicate a gaze direction, an angular distance traveled by an eye, or another eye-related characteristic. For example, an eye-tracking sensor of a wearable device may indicate that an eye's gaze location moved toward a stimulus from its initial gaze location by a distance of 0.3, where the distance may represent an angular distance, a Euclidean distance, or a distance in an eye-related coordinate system. Furthermore, some embodiments may collect additional feedback information, such as a head movement, a sound, etc.

Some embodiments may update a visual display map or associated ocular anomaly information of an eye based on the feedback information and a set of response criteria, as indicated by block 350 of the process 300. Some embodiments may update a visual display map to indicate that an eye is responsive to stimuli or not responsive to stimuli based on a set of criteria. For example, after a stimulus is presented at a field location, some embodiments may indicate that the field location was not seen and associate the field location with an ocular anomaly based on a determination that the later-collected feedback information does not satisfy a set of response criteria. The indication of an ocular anomaly may be stored as a part of a visual field map, which may be used to store ocular anomaly information that indicates which positions or regions of an eye's visual field are healthy and which regions of an eye's visual field are associated with one or more ocular anomalies.

Some embodiments may determine that feedback information collected by a set of eye-tracking sensors satisfies a set of response criteria by determining that an eye's gaze has entered a visual field region mapped to the display region of an external display. For example, some embodiments may present a first stimulus at a wearable display location that causes an eye's gaze to be fixed at a first wearable display location. Some embodiments may then present a second stimulus at an external display location of a first external display. The feedback information may then indicate that the eye's gaze had focused on a region of the first external display. In response, some embodiments may determine that the feedback information collected by the set of eye-tracking sensors satisfies a criterion indicating that the eye has seen the second stimulus. As described elsewhere in this disclosure, some embodiments may then update a visual field map of the eye to indicate that the eye can see stimuli presented at locations mapping to the field location.

Some embodiments may determine that an eye has responded to the presentation of a stimulus at a display location based on a determination that the user's eye movement indicates that the gaze of an eye is within a bounding region of a visual field of the eye. In some embodiments, a bounding region of a visual field may define a region of a visual field within which an eye's gaze direction must remain while moving toward a displayed stimulus. For example, a bounding region may include a region between lines equal to or less than a certain number of radians (e.g., 0.6 radians, 0.4 radians, 0.20 radians, or some other number of radians) away from a straight path from an initial gaze location of the eye to a presented stimulus. For example, some embodiments may determine that an eye's gaze remained within a bounding region after a stimulus was presented until the eye's gaze had reached a field location mapped to a display location of an external screen. As described elsewhere in this disclosure, some embodiments may then update ocular anomaly information for an eye or an associated visual field map to indicate that the eye is responsive to stimuli presented at the field location.

Some embodiments may determine that an eye's gaze has moved outside of a bounding region for a presented stimulus. In response, some embodiments may indicate that a visual defect or another type of ocular anomaly is preventing the eye from seeing presented stimulus by updating ocular anomaly information, such as by updating a visual field map storing the anomaly boundaries of one or more ocular anomalies. For example, a periphery stimulus may be presented at an external display location while a user's eye is fixed on a first stimulus at a wearable display location. Even if the eye did not detect the periphery stimulus, the eye may begin to move around as a part of a user's conscious or subconscious behavior. If the movement causes the eye's gaze to exceed the bounding box, some embodiments may indicate that a field location mapped to the external display location may be part of an ocular anomaly even if the gaze of the eye later focuses on the stimulus.

Some embodiments may determine that feedback information collected by a set of eye-tracking sensors satisfies a set of response criteria by determining that an eye has moved at least a threshold distance toward a stimulus or toward a display presenting the stimulus. For example, after an eye's gaze is fixated at a stimulus positioned at the second display location 222, some embodiments may present a second stimulus at the third display location 223. Some embodiments may use a set of eye-tracking sensors to determine whether the eye's gaze moves a threshold distance toward the third display location 223. For example, some embodiments may determine whether the gaze moved at least 60% of the distance between the second display location 222 and the third display location 223, where 60% may be the distance threshold. While the above uses a distance threshold of 60%, some embodiments may use other distance thresholds, such as 40%, 50%, 80%, 90%, or some other number.

Some embodiments may require that different criterion each be satisfied by feedback information for an eye before a determination that the criteria indicating that an ocular anomaly is or is not present is satisfied by feedback information. For example, some embodiments may present a first stimulus at an external display location of an external display and determine that an eye's gaze must move within a bounding region until the gaze is within a display region corresponding with the screen of the external display. Alternatively, or in addition, some embodiments may permit the satisfaction of different combinations of criteria to update ocular anomaly information for an eye or an associated visual field map. For example, some embodiments may determine that a field location of an eye is capable of detecting stimuli presented on a display if either the eye's gaze stays within a bounding region and reaches a display region mapped to the display or the eye's gaze moves a threshold distance in the direction of the stimulus.

In some embodiments, the set of response criteria may represent indications of eye-related conditions based on color or brightness. For example, a sequence of stimuli displayed on an external display over time may be shown with changing brightness that gets darker or lighter each time a stimulus of the stimuli sequence is presented on the external display. Alternatively, or in addition, presenting a sequence of stimuli may include presenting a stimulus that is shown with a first color and is then shown with a second color. Some embodiments may determine which brightness values or colors induce eye motion and store these values in association with a visual field position mapped to the display location or a visual field region associated with the mapped visual field position. For example, some embodiments may present a stimulus on an external display that changes from a first brightness to a second brightness and collect eye-related characteristics during the brightness change to determine if the eye responds to the brightness change. Based on a determination that the eye responds to the brightness change, some embodiments may update ocular anomaly information or an associated visual field map based feedback information collected during or after the brightness change. For example, some embodiments may determine that an eye's gaze moved from an initial gaze location to the display location of the brightness-modified stimulus and, in response, update a visual field map of the eye to indicate that the eye is responsive to changes in brightness at the field location mapped to the display location. Some embodiments may perform similar operations described above to change the color of stimuli and update a visual field map to indicate that an eye is or is not responsive to color changes for the tested set of colors at a field location.

Some embodiments may use a machine learning model to detect the presence of an ocular anomaly. For example, some embodiments may provide eye-tracking data for an eye, other feedback information, or a visual field map of the eye to a convolutional neural network trained to detect one or more ocular anomalies associated with the eye. The convolutional neural network may perform operations to determine an anomaly boundary of an ocular anomaly, such as the shape of a defective area (e.g., a blind spot or other visual defect) in the peripheral region of an eye. Some embodiments may then use the predicted anomaly boundary to determine a future field location to test. For example, some embodiments may determine whether the anomaly boundary overlaps with a stimuli boundary of a first display region and present a second stimulus on a neighboring region of the first display region. Some embodiments may then perform an additional measurement to update the anomaly boundary of the ocular anomaly based on additional feedback information collected after the presentation of the second stimulus.

Some embodiments may repeat one or more of the operations described above based on a sequence of field locations. For example, some embodiments may perform operations described above to generate a corresponding sequence of display locations, where the sequence of display locations may be updated in real time based on updates to a field-to-display map to display stimuli on a device display of the wearable device or an external display. For example, some embodiments may obtain a visual field sequence that prioritizes a first field location over a second field location, where the first and second field locations are consecutive. Some embodiments may then determine a first display location based on a first field location and a field-to-display map updated at a first time and determine a second display location based on a second field location and the field-to-display map after the map was updated at a second time. In some embodiments, the first display location may be an external display location, and the second display location may be a wearable device location. Some embodiments may then display a first stimulus at the first display location at the first time and then display a second stimulus at the second display location of a wearable device display at the second time.

For each generated stimulus, some embodiments may perform operations to determine whether the feedback information indicating a set of eye-related characteristics satisfies a set of response criteria and update ocular anomaly information for an eye, such as by updating a visual field map. For example, some embodiments may generate a visual field map for an eye based on feedback information collected after the presentation of a first and second stimulus on a first external display and a wearable device display that stretches 150 degrees across a horizontal direction with respect to the eye. Some embodiments may then present a third stimulus at a third display location associated with a field location that is 160 degrees in the horizontal direction from a current gaze location of the eye and expand the dimensions of the visual field map based on a determination that the eye responded to the presence of the third stimulus.

Figure 4:
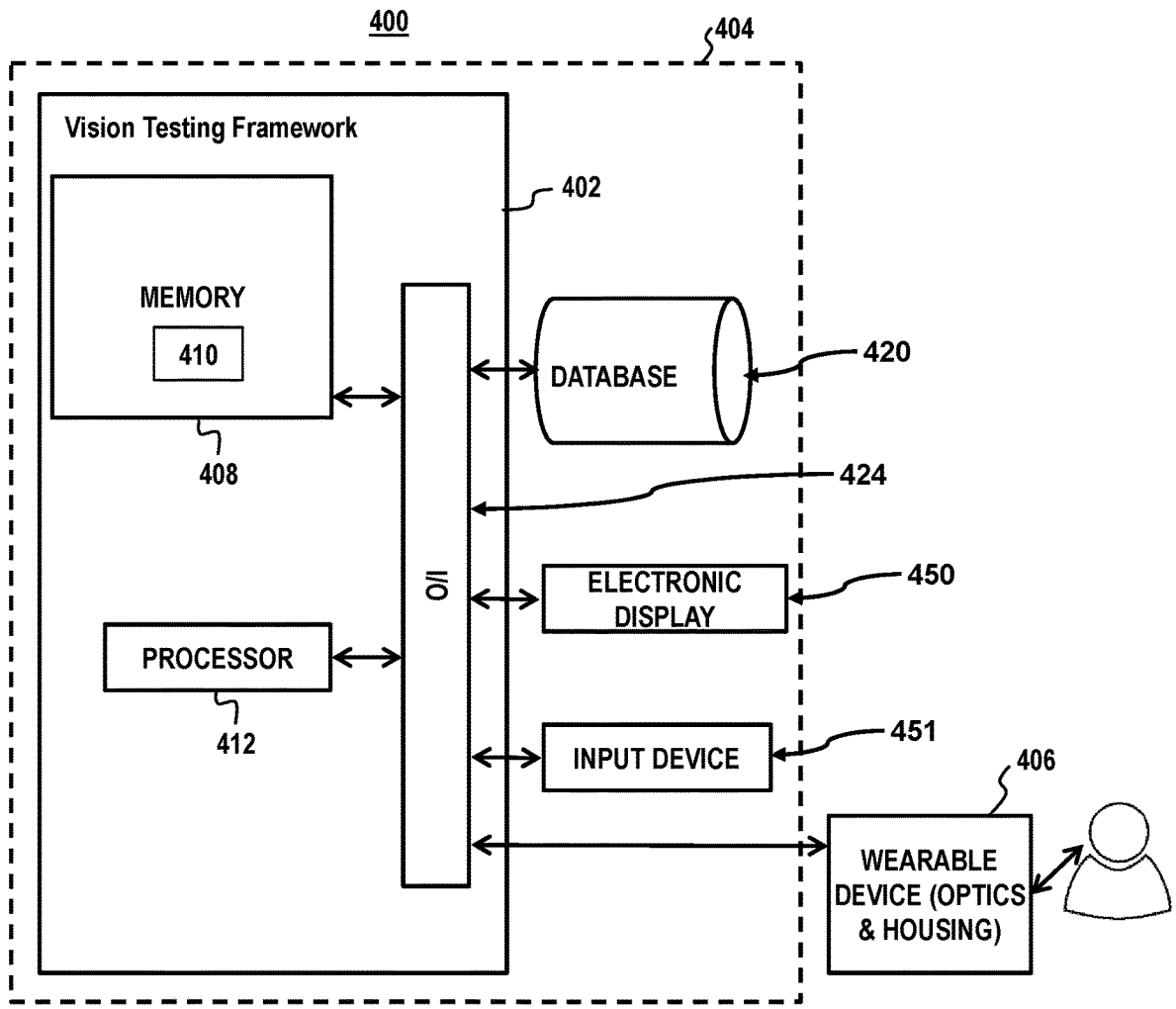
FIG. 4 illustrates a system with a testing framework implemented on a computer device, a wearable device, and a display device, in accordance with one or more embodiments.

In some embodiments, with respect to FIG. 4, system 100 may include a vision system 400, which includes a vision testing framework 402. The vision testing framework 402 may be implemented on an image processing device 404 and a wearable device 406 for placing on a subject. The image processing device 404 may be contained entirely in an external image processing device or other computer, while in other examples all or part of the image processing device 404 may be implemented within the wearable device 406.

The image processing device 404 may include a memory 408 storing instructions 410 that, when executed by the processor 412, for executing the testing and/or visioning modes described herein, may include instructions for collecting feedback information from the wearable device 406. In some embodiments, the wearable device 406 may capture real-time visual field image data as raw data, processed data, or pre-processed data. In some embodiments, a wearable device display of the wearable device 406 may be positioned in front of an eye and may present stimuli, such as characters, images, or other objects, where the eye's response may be used to generate or update a visual field map for the eye.

The wearable device 406 may be communicatively connected to the image processing device 404 through a wired or wireless link. The link may be through a Universal Serial Bus (USB), IEEE 1394 (Firewire), Ethernet, or other wired communication protocol device. The wireless connection can be through any suitable wireless communication protocol, such as WiFi, NFC, iBeacon, Bluetooth, Bluetooth low energy, etc.

In various embodiments, the image processing device 404 may have a controller operatively connected to a database 420 via a link connected to an input/output (I/O) circuit 424. Additional databases may be linked to the controller in a known manner. The controller may include a program memory, the processor 412 (may be called a microcontroller or a microprocessor), a random-access memory (RAM), and the I/O circuit 424, all of which may be interconnected via an address/data bus. It should be appreciated that although only one microprocessor is described, the controller may include multiple microprocessors. Similarly, the memory of the controller may include multiple RAMs and multiple program memories. The RAM(s) and the program memories may be implemented as semiconductor memories, magnetically readable memories, and/or optically readable memories. The link may operatively connect the controller to the capture device, through the I/O circuit 424.

The program memory and/or the RAM may store various applications (i.e., machine readable instructions) for execution by the microprocessor. For example, an operating system may generally control the operation of the vision system 400 such as operations of the wearable device 406 and/or image processing device 404 and, in some embodiments, may provide a user interface to the device to implement the processes described herein. The program memory and/or the RAM may also store a variety of subroutines for accessing specific functions of the image processing device 404 described herein. By way of example, and without limitation, the subroutines may include, among other things: obtaining, from a spectacles device, high-resolution images of a visual field; enhancing and/or correcting the images; and providing the enhanced and/or corrected images for presentation to the subject by the wearable device 406.

In addition to the foregoing, the image processing device 404 may include other hardware resources. The device may also include or be connected to various types of I/O hardware such as an electronic display 450 and an input device 451, where the input device 451 may include devices such as keypads, keyboards, etc. In some embodiments, the electronic display 450 may be touch-sensitive and may cooperate with a software keyboard routine as one of the software routines to accept user input. It may be advantageous for the image processing device 404 to communicate with a broader network (not shown) through any of a number of known networking devices and techniques (e.g., through a computer network such as an intranet, the Internet, etc.). For example, the device may be connected to a database of ocular anomaly data.

The operations of each method presented in this disclosure are intended to be illustrative and non-limiting. It is contemplated that the operations or descriptions of FIG. 3 may be used with any other embodiment of this disclosure. In addition, the operations and descriptions described in relation to FIG. 3 may be done in alternative orders or in parallel to further the purposes of this disclosure. For example, each of these operations may be performed in any order, in parallel, or simultaneously to reduce lag or increase the speed of a computer system or method. In some embodiments, the methods may be accomplished with one or more additional operations not described, and/or without one or more of the operations discussed. Additionally, the order in which the processing operations of the methods are illustrated (and described below) is not intended to be limiting.

In some embodiments, the operations described in this disclosure may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on a non-transitory, machine-readable medium, such as an electronic storage medium. The processing devices may include one or more devices configured through hardware, firmware, and/or software to be specifically designed for execution of one or more of the operations of the methods. For example, it should be noted that any of the devices or equipment discussed in relation to FIG. 1A or FIG. 4 could be used to perform one or more of the operations in FIG. 3.

It should be noted that the features and limitations described in any one embodiment may be applied to any other embodiment herein, and a flowchart or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

In some embodiments, the various computer systems and subsystems illustrated in FIG. 1A or FIG. 4 may include one or more computing devices that are programmed to perform the functions described herein. The computing devices may include one or more electronic storages (e.g., the set of databases 130), one or more physical processors programmed with one or more computer program instructions, and/or other components. The computing devices may include communication lines or ports to enable the exchange of information with a set of networks (e.g., network 150) or other computing platforms via wired or wireless techniques. The network may include the Internet, a mobile phone network, a mobile voice or data network (e.g., a 5G or LTE network), a cable network, a public switched telephone network, or other types of communications networks or combinations of communications networks. The network 150 may include one or more communications paths, such as Ethernet, a satellite path, a fiber-optic path, a cable path, a path that supports Internet communications (e.g., IPTV), free-space connections (e.g., for broadcast or other wireless signals), WiFi, Bluetooth, near field communication, or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Each of these devices described in this disclosure may also include electronic storages. The electronic storages may include non-transitory storage media that electronically stores information. The storage media of the electronic storages may include one or both of (i) system storage that is provided integrally (e.g., substantially non-removable) with servers or client devices, or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). An electronic storage may store software algorithms, information determined by the processors, information obtained from servers, information obtained from client devices, or other information that enables the functionality as described herein.

The processors may be programmed to provide information processing capabilities in the computing devices. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 122-125 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 122-125 described herein is for illustrative purposes, and is not intended to be limiting, as any of subsystems 122-125 may provide more or less functionality than is described. For example, one or more of subsystems 122-125 may be eliminated, and some or all of its functionality may be provided by other ones of subsystems 122-125. As another example, additional subsystems may be programmed to perform some or all of the functionality attributed herein to one of subsystems 122-125.

With respect to the components of computer devices described in this disclosure, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing, storage, and/or input/output circuitry. Further, some or all of the computer devices described in this disclosure may include a user input interface and/or user output interface (e.g., a display) for use in receiving and displaying data. In some embodiments, a display such as a touchscreen may also act as user input interfaces. It should be noted that in some embodiments, one or more devices described in this disclosure may have neither user input interface nor displays and may instead receive and display content using another device (e.g., a dedicated display device such as a computer screen and/or a dedicated input device such as a remote control, mouse, voice input, etc.). Additionally, one or more of the devices described in this disclosure may run an application (or another suitable program) that performs one or more operations described in this disclosure.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment may be combined with one or more features of any other embodiment.

As used throughout this application, the word "may" is used in a permissive sense (i.e., meaning having the potential to), rather than the mandatory sense (i.e., meaning must). The words "include," "including," "includes" and the like mean including, but not limited to. As used throughout this application, the singular forms "a," "an," and "the" include plural referents unless the context clearly indicates otherwise. Thus, for example, reference to "an element" or "a element" includes a combination of two or more elements, notwithstanding use of other terms and phrases for one or more elements, such as "one or more." The term "or" is non-exclusive (i.e., encompassing both "and" and "or"), unless the context clearly indicates otherwise. Terms describing conditional relationships (e.g., "in response to X, Y," "upon X, Y," "if X, Y," "when X, Y," and the like) encompass causal relationships in which the antecedent is a necessary causal condition, the antecedent is a sufficient causal condition, or the antecedent is a contributory causal condition of the consequent (e.g., "state X occurs upon condition Y obtaining" is generic to "X occurs solely upon Y" and "X occurs upon Y and Z"). Such conditional relationships are not limited to consequences that instantly follow the antecedent obtaining, as some consequences may be delayed, and in conditional statements, antecedents are connected to their consequents (e.g., the antecedent is relevant to the likelihood of the consequent occurring). Statements in which a plurality of attributes or functions are mapped to a plurality of objects (e.g., one or more processors performing steps/operations A, B, C, and D) encompass both all such attributes or functions being mapped to all such objects and subsets of the attributes or functions being mapped to subsets of the attributes or functions (e.g., both all processors each performing steps/operations A-D, and a case in which processor 1 performs step/operation A, processor 2 performs step/operation B and part of step/operation C, and processor 3 performs part of step/operation C and step/operation D), unless otherwise indicated. Further, unless otherwise indicated, statements that one value or action is "based on" another condition or value encompass both instances in which the condition or value is the sole factor and instances in which the condition or value is one factor among a plurality of factors.

Unless the context clearly indicates otherwise, statements that "each" instance of some collection have some property should not be read to exclude cases where some otherwise identical or similar members of a larger collection do not have the property (i.e., each does not necessarily mean each and every). Limitations as to sequence of recited steps should not be read into the claims unless explicitly specified (e.g., with explicit language like "after performing X, performing Y"), in contrast to statements that might be improperly argued to imply sequence limitations (e.g., "performing X on items, performing Y on the X'ed items") used for purposes of making claims more readable rather than specifying sequence. Statements referring to "at least Z of A, B, and C" and the like (e.g., "at least Z of A, B, or C") refer to at least Z of the listed categories (A, B, and C) and do not require at least Z units in each category. Unless the context clearly indicates otherwise, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Furthermore, indicated otherwise, updating an item may include generating the item or modifying an existing time. Thus, updating a record may include generating a record or modifying the value of already-generated value.

Enumerated Embodiments

The present techniques will be better understood with reference to the following enumerated embodiments:

1. A method comprising: obtaining spatial information indicating one or more positions of one or more electronic displays relative to a wearable device; determining a first display location on an electronic display other than a wearable display of the wearable device based on the spatial information; determining a second display location based on the spatial information; causing presentation of (i) a first stimulus at the first display location on the electronic display and (ii) a second stimulus at the second display location; and generating ocular anomaly information based on feedback information related to the presented stimuli.
2. The method of embodiment 1, wherein determining the first display location comprises selecting the first display location based on the spatial information indicating that the first display location on the electronic display corresponds to a first field location of a visual field.
3. The method of any of embodiments 1 to 2, wherein the second display location is on the wearable device.
4. The method of any of embodiments 1 to 3, wherein determining the second display location comprises selecting the second display location based on the spatial information indicating that the second display location on the wearable display corresponds to a second field location of the visual field.
5. A method comprising: obtaining, via one or more sensors, spatial information indicating one or more positions of one or more electronic displays relative to a wearable device; updating, based on the spatial information, a map indicating associations between first field locations of a visual field and display locations of an external display; selecting, for a visual test, a first display location on an electronic display other than a wearable display of the wearable device based on the map indicating an association between a first field location of the visual field to be tested during the visual test and the first display location of the electronic display; selecting, for the visual test, a second display location on the wearable device based on the map indicating an association between a second field location of the visual field to be tested and the second display location of the wearable device; causing, during the visual test, a presentation of (i) a first stimulus at the first display location on the electronic display and (ii) a second stimulus at the second display location on the wearable device; and generating ocular anomaly information based on feedback information related to the presented stimuli.
6. A method comprising: collecting sensor information comprising relative spatial information indicating orientation and positions of one or more external displays relative to the wearable device using one or more sensors; continuously updating, based on the relative spatial information, a field-to-display map indicating (i) associations between field locations of a visual field and external display locations of one or more external displays and (ii) associations between field locations of the visual field and wearable display locations of a wearable display of the wearable device; selecting an external display location of an external display as a corresponding display location for a first field location of the visual field in response to (i) a field location sequence indicating the first field location to be tested at a first time and (ii) the field-to-display map indicating an association between the first field location and the external display location; selecting a wearable display location of the wearable device as a corresponding display location for a second field location of the visual field in response to (i) the field location sequence indicating the second field location to be tested at a second time and (ii) the field-to-display map indicating an association between the second field location and the wearable display location; causing presentation of (i) a stimulus at the external display location associated with the first field location at the first time and (ii) a stimulus at the wearable display location associated with the second field location at the second time; and generating ocular anomaly information based on feedback information related to the presented stimuli.

7. The method of any of embodiments 1 to 6, wherein a stimuli boundary surrounds a region of the visual field associated with the external display, further comprising: determining that the first field location is associated with an ocular anomaly identified by the ocular anomaly information before the presentation of the stimulus at the external display location; and determining whether the first field location is within a distance threshold of the stimuli boundary, wherein presenting the stimulus at the external display location comprises presenting the stimulus at the external display location in response to a determination that the first field location is within the distance threshold of the stimuli boundary.

8. The method of any of embodiments 1 to 7, further comprising: detecting, between the presentation of the first stimulus at the external display location and the presentation of the stimulus at the wearable display location, a rotation or translation of the wearable device; and updating the field-to-display map based on the rotation or translation of the wearable device, wherein presenting the stimulus at the external display location comprises using the updated field-to-display map.

9. The method of any of embodiments 1 to 8, further comprising: providing first feedback information to a prediction model to detect an ocular anomaly identified by the ocular anomaly information and an anomaly boundary associated with the ocular anomaly, wherein the first feedback information is collected during or after the presentation of the first stimulus and is collected before the presentation of the second stimulus; and determining whether the anomaly boundary overlaps with a stimuli boundary of the electronic display, wherein causing the presentation of the second stimulus comprises causing the presentation of the second stimulus based on a determination that the anomaly boundary overlaps with the stimuli boundary.

10. The method of any of embodiments 1 to 9, wherein generating the ocular anomaly information comprises: determining whether a gaze location moved from a first visual field region associated with the electronic display to a second visual field region associated with the wearable display; and updating a visual field map to indicate that stimuli presented at the second field location are detectable based on a determination that the gaze location moved from the first visual field region to the second visual field region.

11. The method of any of embodiments 1 to 10, wherein presenting the second stimulus comprises presenting the second stimulus with a shape having a second stimulus length associated with the second stimulus, the method further comprising: determining a distance between the wearable device and the electronic display; and determining a first stimulus length by scaling the second stimulus length by the distance, wherein the first stimulus is presented based on the first stimulus length.

12. The method of any of embodiments 1 to 11, wherein the electronic display is a first electronic display, further comprising: presenting a third stimulus on a second electronic display of a second display device; collecting additional feedback information during or after presenting of the third stimulus; and expanding a dimension of a visual field map of the visual field based on the additional feedback information.

13. The method of any of embodiments 1 to 12, wherein the feedback information comprises a gaze direction and a distance traveled in the gaze direction, and wherein generating the ocular anomaly information comprises: determining whether the distance satisfies a distance threshold; and in response to a determination that the distance satisfies the distance threshold, updating a visual field map of the visual field to indicate that an eye is responsive to stimuli associated with the second field location.

14. The method of any of embodiments 1 to 13, wherein presenting the first stimulus comprises: presenting the first stimulus with a first brightness; presenting the first stimulus with a second brightness; and collecting a portion of the feedback information during the change in the brightness.

15. The method of any of embodiments 1 to 14, wherein presenting the first stimulus comprises: presenting the first stimulus with a first color; presenting the first stimulus with a second color; and collecting a portion of the feedback information during the change in the color.

16. The method of any of embodiments 1 to 15, wherein generating the ocular anomaly information comprises: determining a bounding region of the visual field, wherein the bounding region is between lines equal to a certain number of radians away from a straight path from the first field location to the second field location; determining whether a gaze location remains within the bounding region as the gaze location moves toward the second field location; and detecting an ocular anomaly based on a determination that the gaze location does not remain within the bounding region as the gaze location moves toward the second field location.

17. The method of any of embodiments 1 to 16, further comprising: presenting an initial stimulus before the presentation of the first stimulus, wherein an eye-tracking sensor obtains a set of eye-related characteristics after the presentation of the initial stimulus; and updating the map based on the set of eye-related characteristics, wherein selecting the first display location comprises selecting the first display location based on the updated map.

18. The method of any of embodiments 1 to 17, wherein the electronic display is a first electronic display, further comprising: presenting a set of stimuli on a plurality of electronic displays, wherein each respective stimulus of the set of stimuli is presented on a respective electronic display of the plurality of electronic displays, and wherein the plurality of electronic displays comprises the first electronic display; updating the feedback information based on sensor information obtained by eye-tracking sensors during or after the presentation of each stimulus of the set of stimuli; and updating a visual field map of the visual field based on the updated feedback information.

19. The method of any of embodiments 1 to 18, wherein generating the ocular anomaly information comprises: providing the feedback information to a machine learning model; and detecting an ocular anomaly based on an output of the machine learning model.

20. The method of any of embodiments 1 to 19, wherein the electronic display is a first electronic display, further comprising presenting a calibration stimulus at the second display location before presenting the first stimulus.

21. The method of any of embodiments 1 to 20, wherein the electronic display is a first electronic display, further comprising presenting a third stimulus on the first electronic display by: determining a candidate set of field locations separated from the second field location by at least a distance threshold, wherein at least one location of the candidate set of field locations is mapped to a third display location on a second electronic display other than the wearable display; selecting a third field location from the candidate set of field locations based on a random or pseudorandom value; and displaying the third stimulus on the second electronic display at a third display location mapped to the third field location.

22. The method of any of embodiments 1 to 21, further comprising: presenting a set of calibration stimuli on the electronic display; determining a set of distance measurements based on the set of calibration stimuli; and determining the position and orientation of the electronic display based on the set of distance measurements.

23. The method of any of embodiments 1 to 22, wherein selecting the first display location comprises: determining a candidate set of field locations; obtaining a boundary of a viewable region based on a visual field map of the visual field; updating the candidate set of field locations based on the boundary and the candidate set of field locations by removing a candidate field location from the candidate set of field locations based on a determination that the candidate field location is not in the viewable region, wherein the updated candidate set of field locations comprises the first display location; and selecting the first display location from the updated candidate set of field locations.

24. One or more tangible, non-transitory, machine-readable media storing instructions that, when executed by one or more processors, effectuate operations comprising those of any of embodiments 1 to 23.

25. A system comprising: one or more processors; and memory storing computer program instructions that, when executed by the one or more processors, cause the one or more processors to effectuate operations comprising those of any of embodiments 1 to 23.

A wearable device comprising: one or more sensors for collecting sensor information comprising relative spatial information indicating orientation and positions of one or more external displays relative to a wearable display of the wearable device; and one or more processors executing computer program instructions that, when executed, cause the one or more processors to effectuate operations comprising those of any of embodiments 1 to 23.

What is claimed is:

1. A wearable device for ocular anomaly detection via mapping visual field locations to display locations on both a wearable device display and external displays, comprising: one or more sensors for collecting sensor information comprising relative spatial information indicating orientation and positions of one or more external displays relative to the wearable device; one or more processors executing computer program instructions that, when executed, cause operations comprising:
continuously updating, based on the relative spatial information, a field-to-display map indicating (i) associations between field locations of a visual field and external display locations of one or more external displays and (ii) associations between field locations of the visual field and wearable display locations of a wearable display of the wearable device;
selecting an external display location of an external display as a corresponding display location for a first field location of the visual field in response to (i) a field location sequence indicating the first field location to be tested at a first time and (ii) the field-to-display map indicating an association between the first field location and the external display location;
selecting a wearable display location of the wearable device as a corresponding display location for a second field location of the visual field in response to (i) the field location sequence indicating the second field location to be tested at a second time and (ii) the field-to-display map indicating an association between the second field location and the wearable display location;
causing presentation of (i) a stimulus at the external display location associated with the first field location at the first time and (ii) a stimulus at the wearable display location associated with the second field location at the second time; and
generating ocular anomaly information based on feedback information related to the presented stimuli.

2. The wearable device of claim 1, wherein a stimuli boundary surrounds a region of the visual field associated with the external display, the operations further comprising:
determining that the first field location is associated with an ocular anomaly identified by the ocular anomaly information before the presentation of the stimulus at the external display location; and
determining whether the first field location is within a distance threshold of the stimuli boundary, wherein presenting the stimulus at the external display location comprises presenting the stimulus at the external display location in response to a determination that the first field location is within the distance threshold of the stimuli boundary.

3. The wearable device of claim 1, the operations further comprising:
detecting, between the presentation of the stimulus at the external display location and the presentation of the stimulus at the wearable display location, a rotation or translation of the wearable device; and
updating the field-to-display map based on the rotation or translation of the wearable device, wherein presenting the stimulus at the external display location comprises using the updated field-to-display map.

4. A method comprising:
obtaining, via one or more sensors, spatial information indicating one or more positions of one or more electronic displays relative to a wearable device;
updating, based on the spatial information, a map indicating associations between first field locations of a visual field and display locations of an external display;
selecting, for a visual test, a first display location on an electronic display other than a wearable display of the wearable device based on the map indicating an association between a first field location of the visual field to be tested during the visual test and the first display location of the electronic display;

selecting, for the visual test, a second display location on the wearable device based on the map indicating an association between a second field location of the visual field to be tested and the second display location of the wearable device;

causing, during the visual test, a presentation of (i) a first stimulus at the first display location on the electronic display and (ii) a second stimulus at the second display location on the wearable device; and generating ocular anomaly information based on feedback information related to the presented stimuli.

5. The method of claim 4, further comprising:
providing first feedback information to a prediction model to detect an ocular anomaly identified by the ocular anomaly information and an anomaly boundary associated with the ocular anomaly, wherein the first feedback information is collected during or after the presentation of the first stimulus and is collected before the presentation of the second stimulus; and
determining whether the anomaly boundary overlaps with a stimuli boundary of the electronic display, wherein causing the presentation of the second stimulus comprises causing the presentation of the second stimulus based on a determination that the anomaly boundary overlaps with the stimuli boundary.

6. The method of claim 4, wherein generating the ocular anomaly information comprises:
determining whether a gaze location moved from a first visual field region associated with the electronic display to a second visual field region associated with the wearable display; and
updating a visual field map to indicate that stimuli presented at the second field location are detectable based on a determination that the gaze location moved from the first visual field region to the second visual field region.

7. The method of claim 4, wherein presenting the second stimulus comprises presenting the second stimulus with a shape having a second stimulus length associated with the second stimulus, the method further comprising:
determining a distance between the wearable device and the electronic display; and
determining a first stimulus length by scaling the second stimulus length by the distance, wherein the first stimulus is presented based on the first stimulus length.

8. The method of claim 4, wherein the electronic display is a first electronic display, further comprising:
presenting a third stimulus on a second electronic display of a second display device;
collecting additional feedback information during or after presenting of the third stimulus; and
expanding a dimension of a visual field map of the visual field based on the additional feedback information.

9. The method of claim 4, wherein the feedback information comprises a gaze direction and a distance traveled in the gaze direction, and wherein generating the ocular anomaly information comprises:
determining whether the distance satisfies a distance threshold; and
in response to a determination that the distance satisfies the distance threshold, updating a visual field map of the visual field to indicate that an eye is responsive to stimuli associated with the second field location.

10. The method of claim 4, wherein:
presenting the first stimulus comprises:
presenting the first stimulus with a first brightness; and
causing a change in brightness of the first stimulus by presenting the first stimulus with a second brightness; and
collecting a portion of the feedback information during the change in the brightness.

11. The method of claim 4, wherein:
presenting the first stimulus comprises:
presenting the first stimulus with a first color; and
causing a change in color of the first stimulus by presenting the first stimulus with a second color; and
collecting a portion of the feedback information during the change in the color.

12. The method of claim 4, wherein generating the ocular anomaly information comprises:
determining a bounding region of the visual field, wherein the bounding region is between lines equal to a certain number of radians away from a straight path from the first field location to the second field location;
determining whether a gaze location remains within the bounding region as the gaze location moves toward the second field location; and
detecting an ocular anomaly based on a determination that the gaze location does not remain within the bounding region as the gaze location moves toward the second field location.

13. The method of claim 4, further comprising:
presenting an initial stimulus before the presentation of the first stimulus, wherein an eye-tracking sensor obtains a set of eye-related characteristics after the presentation of the initial stimulus; and
updating the map based on the set of eye-related characteristics, wherein selecting the first display location comprises selecting the first display location based on the updated map.

14. A non-transitory computer-readable media storing instructions that, when executed by one or more processor, cause operations comprising:
obtaining spatial information indicating one or more positions of one or more electronic displays relative to a wearable device;
selecting a first display location on an electronic display other than a wearable display of the wearable device based on the spatial information indicating that the first display location on the electronic display corresponds to a first field location of a visual field;
selecting a second display location on the wearable device based on the spatial information indicating that the second display location on the wearable display corresponds to a second field location of the visual field;
causing presentation of (i) a first stimulus at the first display location on the electronic display and (ii) a second stimulus at the second display location on the wearable device; and
generating ocular anomaly information based on feedback information related to the presented stimuli.

15. The media of claim 14, wherein the electronic display is a first electronic display, the operations further comprising:
presenting a set of stimuli on a plurality of electronic displays, wherein each respective stimulus of the set of stimuli is presented on a respective electronic display of the plurality of electronic displays, and wherein the plurality of electronic displays comprises the first electronic display; and updating the feedback information based on sensor information obtained by eye-tracking sensors during or after the presentation of each stimulus of the set of stimuli; and updating a visual field map of the visual field based on the updated feedback information.

16. The media of claim 14, wherein generating the ocular anomaly information comprises:

providing the feedback information to a machine learning model; and detecting an ocular anomaly based on an output of the machine learning model.

17. The media of claim 14, wherein the electronic display is a first electronic display, the operations further comprising presenting a calibration stimulus at the second display location before presenting the first stimulus.

18. The media of claim 14, wherein the electronic display is a first electronic display, the operations further comprising presenting a third stimulus on the first electronic display by:

determining a candidate set of field locations separated from the second field location by at least a distance threshold, wherein at least one location of the candidate set of field locations is mapped to a third display location on a second electronic display other than the wearable display;

selecting a third field location from the candidate set of field locations based on a random or pseudorandom value; and displaying the third stimulus on the second electronic display at a third display location mapped to the third field location.

19. The media of claim 14, the operations further comprising:

presenting a set of calibration stimuli on the electronic display;

determining a set of distance measurements based on the set of calibration stimuli; and determining a position and orientation of the electronic display based on the set of distance measurements.

20. The media of claim 14, wherein selecting the first display location comprises:

determining a candidate set of field locations;

obtaining a boundary of a viewable region based on a visual field map of the visual field;

updating the candidate set of field locations based on the boundary and the candidate set of field locations by removing a candidate field location from the candidate set of field locations based on a determination that the candidate field location is not in the viewable region, wherein the updated candidate set of field locations comprises the first display location; and selecting the first display location from the updated candidate set of field locations.

* * * * *